United States Patent [19]

Heidgen

[11] Patent Number: Plant 6,353

[45] Date of Patent: Oct. 25, 1988

[54] GERANIUM PLANT NAMED NIGHT WATCH

[76] Inventor: Charles F. Heidgen, 821 Walnut St., Batavia, Ill. 60510

[21] Appl. No.: 782,734

[22] Filed: Oct. 1, 1985

[51] Int. Cl.[4] ..... A01H 5/00

[52] U.S. Cl. ..... Plt./68

[58] Field of Search ..... Plt./68

*Primary Examiner*—Robert E. Bagwill

[57] ABSTRACT

A new and distinct variety of geranium plant, Night Watch, characterized by its cascading growth habit; its continuous flowering habit; its small to medium-sized, light pink flowers; its striking dark foliage with darker zonation; and its heat tolerance.

1 Drawing Sheet

The present discovery, hereinafter referred to by the cultivar name, Night Watch, relates to a new and distinct geranium plant.

BACKGROUND

Night Watch is a new and improved variety which has resulted from definite breeding programs and experiments carried on by me in my greenhouses at 821 Walnut St., Batavia, Ill. Our experiments commenced in March, 1977 and are being carried on continuously. This seedling, 79×031 M, is the result of a cross between Frank Headley, an unpatented, variagated foliage, dwarf geranium and Red Heart, an unpatented cascade geranium.

Asexual reproduction of Night Watch has been accomplished from vegatative cuttings in my greenhouse in Batavia, Ill. Examination of the plants so propagated has demonstrated that the combination of characteristics herein disclosed for Night Watch are firmly fixed and retained through successive generations of asexual reproduction.

SUMMARY

The new and patentable characteristics of Night Watch reside in its cascading growth habit, its continuous flowering habit, its small to medium-sized light pink flowers, its striking dark foliage with even darker zonation and its heat tolerance.

DESCRIPTION OF DRAWING

The photograph shows the plant and flower of a fully developed geranium of the new variety, Night Watch.

BOTANIC DESCRIPTION

The Plant

Growth: Night Watch is a continuously blooming geranium with a distinctive dark-colored foliage. The flower head (truss) is small to medium-sized, double and resistant to shattering. It has a procumbent, cascading growth habit that is vigorous and allows the plant to become quite large. This geranium is also ethrel responsive. Growth rate is rapid, producing a typical 10″ flowering basket in 10–12 weeks from four 2¼ plants using standard commercial culture.

Blooming habit: A continuous bloomer, throughout the year, outdoors or in the greenhouse with superior blooming performance in exceptionally hot weather. In brighter, sunnier locations the foliage is much darker. There is a paucity of bloom in the short, dark days of winter. A mature, 10″ basket commonly produces 18–26 heads at one time.

Inflorescence: Small to medium-sized, tight head, somewhat rounded, measuring 2¾–3¾ inches in diameter.

Foliage:

*Quantity.*—Abundant.

*Size.*—Medium, 2–2¾ inches across.

*Color.*—Parsley Green (00962) with Ivy Green (0001060) zone (The Royal Horticultural Society Horticultural Colour Chart).

*Texture.*—Smooth, almost waxy.

Stem: Medium slim, normal internodes, free branching, cascading habit.

Petiole: Medium length, 2–2½ inches, same color as leaves.

The Flower

Truss:

*Size.*—Small to medium-size, 2¾–3¾ inches in diameter.

*Shape.*—Roundish, a flattened globe as it opens.

*Number of florets.*—Variable, range from 10–22, average 12–15.

*Lasting quality.*—Average. Blossoms last 5–10 days, longer if cool and dry.

Bud:

*Sepals.*—Narrow, pointed.

*Color.*—Camellia Rose (622/1) (The Royal Horticultural Society Horticultural Colour Chart).

*Form.*—Pointed, roundish.

Florets:

*Size.*—1¼–1⅜ inches across.

*Petalage.*—Double, 9–11.

*Color.*—Fuschine Pink (627/3) (The Royal Horticultural Society Horticultural Colour Chart).

Texture: Light and soft.

Form: Double flower, petals range from ⅓ to ½ inch wide.

Behavior: When this plant begins blooming, it is covered with many small to medium-sized, light pink blossoms that make a striking display against the medium-sized, dark-colored foliage.

Having thus disclosed my invention, I claim:

1. A new and distinct variety of geranium plant, substantially as shown and described, characterized by its cascading growth habit, its continuous flowering habit, its small to medium-sized, light pink flowers, its striking dark foliage with darker zonation and its heat tolerance.

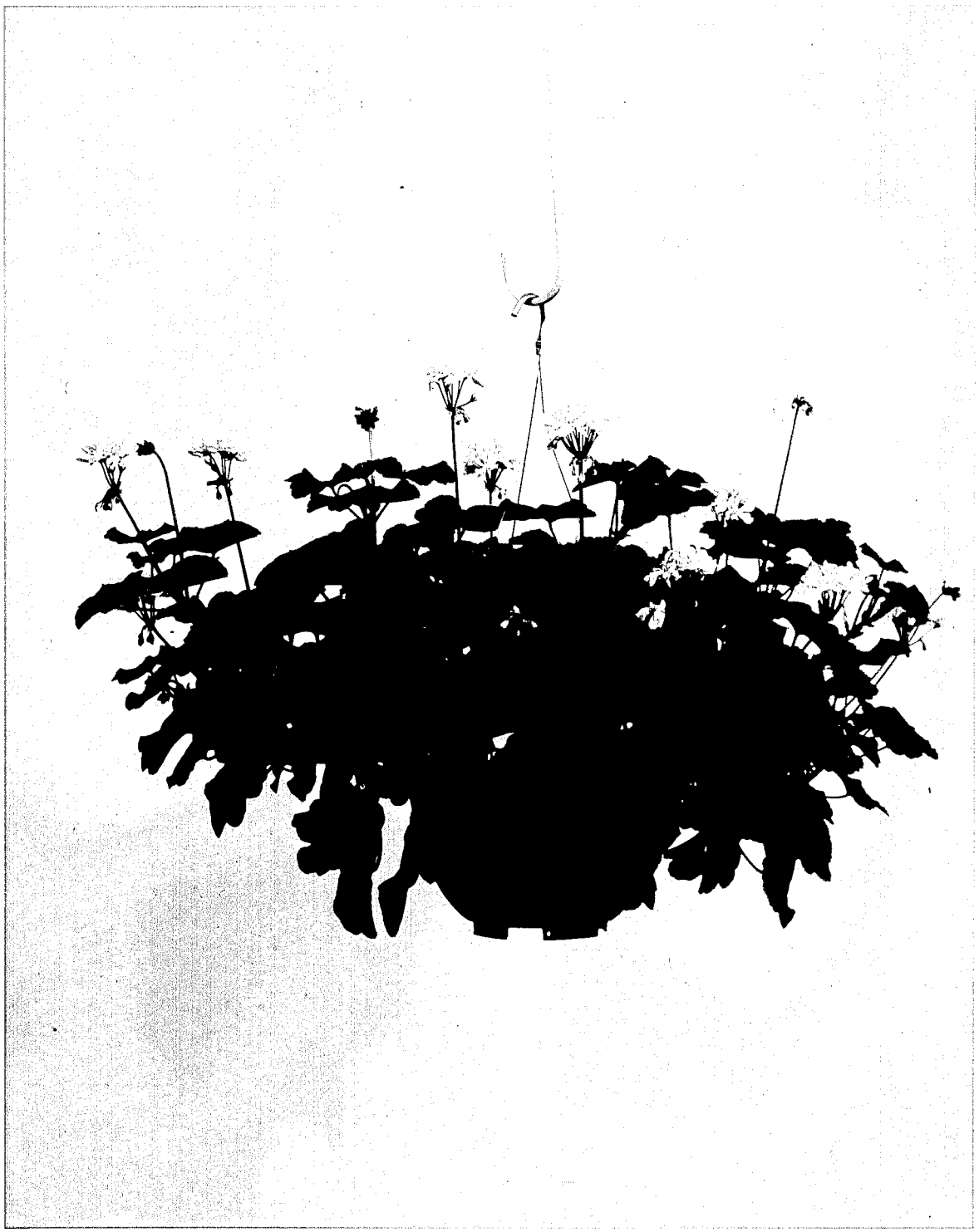

* * * * *